(12) United States Patent
Haas et al.

(10) Patent No.: US 6,593,461 B1
(45) Date of Patent: *Jul. 15, 2003

(54) **ADHERENCE GENE FROM *HELICOBACTER PYLORI* AND POLYPEPTIDE CODED THEREBY**

(75) Inventors: Rainer Haas, Tübingen (DE); Stefan Odenbreit, Ammerbuch (DE); Thomas F. Meyer, Tübingen (DE); André Blum, Romammôtier (CH); Irène Corthésy-Theulaz, Lausanne (CH)

(73) Assignee: Max-Planck-Gesellschaft zur Föderung der Wissenscaften e.v., München (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/973,105

(22) PCT Filed: Jun. 12, 1996

(86) PCT No.: PCT/EP96/02545

§ 371 (c)(1),
(2), (4) Date: Dec. 10, 1997

(87) PCT Pub. No.: WO96/41880

PCT Pub. Date: Dec. 27, 1996

(30) Foreign Application Priority Data

Jun. 12, 1995 (DE) .......................... 195 21 314

(51) Int. Cl.[7] .............................. C07H 21/02
(52) U.S. Cl. .................. 536/23.1; 514/44; 514/562; 435/69.1; 435/70.1; 435/6; 424/94.6; 424/195.1
(58) Field of Search .................. 514/44, 562; 435/69.1, 435/70.1, 6; 536/23.1; 424/94.6, 195.1

(56) References Cited

U.S. PATENT DOCUMENTS

| | | | | |
|---|---|---|---|---|
| 5,545,670 A | * | 8/1996 | Bissbort et al. ............. | 514/562 |
| 5,837,240 A | * | 11/1998 | Lee et al. ................. | 424/94.6 |
| 6,074,818 A | * | 6/2000 | Caetano-anolles et al. ..... | 435/6 |
| 6,096,521 A | * | 8/2000 | Haas et al. ................ | 435/70.1 |

FOREIGN PATENT DOCUMENTS

| | | | | |
|---|---|---|---|---|
| DE | 4020181 A | * | 1/1992 | |
| WO | 96 33732 | * | 10/1996 | |
| WO | 96/41891 | * | 12/1996 | ............ C12Q/1/68 |

OTHER PUBLICATIONS

Amara, A et al, Neuroscience letters, Feb. 13, 1995, vol. 185(3), pp. 147–150 (abstract only).*

Ryder, K et al, Cell, Mar. 14, 1986, vol. 44(6), pp. 719–725, (abstract only).*

Odenbreit, S et al, Molecular Microbiology, vol. 20(2), pp. 361–373, Apr. 1996.*

(List continued on next page.)

Primary Examiner—Lynette R. F. Smith
Assistant Examiner—Ginny Allen Portner
(74) Attorney, Agent, or Firm—Rothwell, Figg, Ernst & Manbeck (57) ABSTRACT

The present invention concerns an adherence gene from *Helicobacter pylori*, a polypeptide coded thereby and antibodies against the polypeptide.

13 Claims, 4 Drawing Sheets

OTHER PUBLICATIONS

Bukanov, N.O. et al, Molecular Microbiology, Feb. 1994, vol. 11(3), pp. 50–523.*
Taylor, D.E et al, Journal of Bacteriology, vol. 174(21), pp. 6800–6806, Nov. 1992.*
Zwicki, P. et al, J. Bacteriol, vol. 172, p 4329–4338, (abstract), 1990.*
Hoshimoto, J., Mol. Gen. Genet., vol. 233 (1–2), p10–16, (abstract), 1992.*
Cameron–Mill, N. et al, Plant Mol. Biol, vol. 11, p 449–461, (abstract), 1988.*
Chesneau, O. et al, Gene, vol. 145, p41–47, (abstract), 1994.*
Moran, A. B, FEMS Immunol. and Med. Microbiol., vol. 10, p271–280, 1995.*
Fauchere, JL et al, Microbial Pathogen., vol. 9, p 427–439, 1990.*
Tomb, J.F et al, Nature, vol. 388, Aug. 7, p 539–547, 1997.*
Perez–Perez, G. et al., Infect.Immun., May vol. 55(5), p 1256–1263, 1987.*
Vijayakumari, S. et al, Cytobios, vol. 82(331), p 251–260, 1995 (abstract).*
Qasem, J., vol. 56(09–B) Dissertation Abstracts Int., p 4737, 63 pages (abstract), 1995.*
Ho, B. et al, Feb., Eur. J. Gastroenterol & Hepat., p 121–124, vol. &(2) (abstract), 1995.*
Lelwala–Guruge, J.A., Doctorial Dissertation, Lund, Oct. 1993, Lumedw/(MEMi–1019) 1–156/1993.*
Segal, E. D. et al, Infect. Agents and Disease, vol. 2, p 178–182, 1994.*
Huang,JZ et al, J. Gen. Microbiol, vol. 138, Jul., p 1503–1513, 1992.*
Evans et al, *Journal of Bacteriology*, Feb. 1993, p. 674–683, "Cloning, nucleotide Sequence, and Expression of a Gene Encoding an Adhesin Subunit Protein of *Helicobacter pylori*".
Wasdström et al., *European Journal of Gastroenterology & Hepatology*, 1993, vol. 5 (suppl. 2), "*Helicobacter pylori* adhesins".
Alkout et al., *GUT*, 17–9 Jul. 1995, 37, supp. 7, p. A21, "Identification of surface components of Helicobacetr pylori that bind H type 2 and Lewis blood group antigens".

* cited by examiner

ADHERENCE GENE FROM *HELICOBACTER PYLORI* AND POLYPEPTIDE CODED THEREBY

DESCRIPTION

The present invention concerns a method for identifying secretory genes and in particular adherence genes from *Helicobacter pylori*. In addition the invention concerns a gene bank suitable for identifying secretory genes from *H. pylori*, polynucleotides and polypeptides a obtainable from this gene bank, in particular the alpA-gene from *Helicobacter pylori* and the polypeptide which it codes. These polynucleotides and polypeptides can be used to diagnose, prevent and treat a Helicobacter infection.

The occurrence of spiral bacteria in the human gastric mucous membrane has been known for a long time (Bizzozero, 1893). The fact that these are pathogenic germs was, however, not realized until the successful isolation and culture of this bacterium by Marshall and Warren (Warren and Marshall, 1983; Marshall et al., 1984) from the gastric mucous membrane of a patient with a gastric ulcer (ulcus ventriculi). As the first analyses showed the isolated microorganisms were gram-negative, spiral bacteria with an extremely high motility and the unusual ability of being able to survive in a strongly acidic environment (up to ca. pH 1.5). The germs which were originally denoted *Campylobacter pylori* were finally classified on the basis of biochemical and morphological characteristics in the newly established genus "Helicobacter" (Goodwin et al., 1989).

The importance of *Helicobacter pylori* infection and the implications of this discovery already became clear within a few years. Epidemiological investigations by Taylor and Blaser (1991) showed that the *H. pylori* infection occurs world-wide and that ca. 50% of the population are infected with this bacterium, the infection rate being higher in the developing countries than in industrialized countries. Furthermore it was observed that the probability of a chronic *H. pylori* infection increases drastically with increasing age. Hence the *H. pylori* infection is among the most frequent chronic bacterial infections of humans.

Today it is known that the infection inevitably leads to the induction of a bacterial gastritis (type B gastritis) in humans. Moreover it is assumed that *H. pylori* also plays a causal role in the development of gastric and duodenal ulcers (ulcus ventriculi and ulcus duodeni) as well as some forms of gastric carcinoma (adenocarcinoma) (Lee et al., 1993; Solnick and Tompkins, 1993). Even the MALT (mucosa associated lymphoid tissue) lymphomas of the stomach which occur more rarely and are regarded as a precursor of B cell tumours of the immune system are also presumably a result of *H. pylori* infection. An antibacterial treatment of such patients with the successful eradication (total elimination) of *H. pylori* leads to a healing of gastric ulcers as well as of low grade MALT lymphomas (Sipponen and Hyvärinen, 1993; Isaacson and Spencer, 1993; Stolte and Eidt, 1993).

A sequel of a long-term infection with *H. pylori* is atrophic gastritis, a degeneration of the mucous, acid or pepsin-producing cells of the stomach epithelium which has to be regarded as a pre-cancerous lesion. According to statistics of the types of cancer which occurred world-wide most frequently in 1980, gastric carcinoma is in second place but with a declining tendency (Parkin et al., 1988). Two studies have recently shown a statistically significant correlation between *H. pylori* infection and the occurrence of gastric carcinoma (intestinal type); both came to the conclusion that ca. 60% of all gastric carcinomas that occur are probably due to a *H. pylori* infection (Parsonnet et al., 1991; Nomura et al., 1991). Furthermore investigations by Sipponen (1992) show that in many industrialized countries more than 20% of infected persons contract an ulcer of the stomach or of the duodenum during their life whereas this risk is negligibly small in persons with a normal gastric mucosa. This means that these frequent gastro-duodenal diseases must be regarded as infectious diseases and treated appropriately (Alper, 1993). A treatment which eliminates a chronic *H. pylori* infection that is already present leads to a healing of a gastritis, a gastric or duodenal ulcer or a MALT lymphoma. Thus a prophylactic treatment which prevents a *H. pylori* infection (e.g. immunization) as well as a treatment which eliminates a *H. pylori* infection that is already present can be used to treat these frequent gastro-duodenal diseases.

Apart from some higher primates, humans were previously the only known natural host for *H. pylori*. The relatively recent discovery that the domestic cat can also be infected with *H. pylori* throws new light onto the question of transmission and a possible reservoir for the bacteria outside the human organism. The occasionally successful culture of *H. pylori* from the faeces of infected persons and the ability of the bacteria to survive for months in water support the hypothesis of a faecal-oral transmission. Also direct oral-oral transmission is regarded as probable on the basis of family studies. The infection usually occurs in childhood within the family, cramped living conditions and a poor standard of hygiene correlating positively with the frequency of the infection.

After oral uptake the bacteria first reach the extremely acid stomach lumen (pH 1–2). Here the survival of the bacteria is made possible by the production of the enzyme urease which leads to cleavage of the urea that is present and thus to a local neutralization of the acidic pH value in the stomach. By means of chemotactic orientation and flagella-dependent motility the microorganisms then move into the bicarbonate-buffered mucosal layer of the antrum region of the stomach which is in fact their natural habitat. Here they are in a unique ecological niche which, due to the acid barrier, is accessible only to a few competing bacterial species. The microorganisms presumably orientate themselves by means of the pH gradient between the lumen (pH 1–2) and epithelial cell surface (pH 6–7) in order to reach the epithelium. Due to their spiral shape, their motility in viscous mucous, the production of mucous-modifying enzymes and finally their microaerophilic way of living, these germs are optimally adapted to the living conditions in this habitat.

They usually spend their time in the deep crypts of the antrum region where they are protected from external influences such as e.g. acid, pepsin and also from medicines for their eradication such as e.g. antibiotics. Part of the population (ca. 20%) is closely associated with epithelial cells especially with mucous-producing cells. Under the condition of a gastral metaplasia i.e. the acid-induced formation of gastral epithelium in the duodenum, the metaplastic areas in the duodenum are also colonized which creates the prerequisites for the development of a duodenal ulcer (ulcus duodeni). A complete excretion of the Helicobacter with the shed mucous is probably prevented by their ability to adhere so that the bacteria can persist for years, decades or even for a life time (chronic infection).

Before the existence and the significance of *H. pylori* for ulcerous diseases was known, these were treated with so-called antacids or $H_2$-receptor antagonists. These are substances which inhibit the acid secretion of the parietal cells of the stomach. The action of these pharmaceutical agents usually leads to a healing of the ulcers but, since one of the causes of these ulcers i.e. *H. pylori* infection, is not eliminated by this, in most cases a re-occurrence of the ulceration (relapse) occurs within a short period.

A further frequently used therapy in ulcerations is bismuth treatment. Various bismuth salts (CBS, BSS) have a bactericidal effect on *H. pylori*. However, a total eradication of these germs is only achieved in 8–32% of the cases. The treatment apparently leads to a temporary suppression of the germs but after discontinuing the treatment the infection flares up again in most cases. A long-term therapy with high doses leads to an accumulation of the substance in the liver, kidney and nervous system and has considerable neurological side-effects (Malfertheiner, 1994).

Since it has been discovered that gastroduodenal ulcer diseases are infectious diseases, one aim of treatment is to eradicate the pathogens by antibiotics. Monotherapy with various antibiotics (amoxicillin, nitrofuran, furazolidin, erythromycin a.o.) has, however, turned out not to be satisfactory since even in this case eradication of the germs only occurs in 0–15% of the cases. The most successful treatment at the moment is achieved by a combination of an acid blocker (Ompeprazol) with an antibiotic (Amoxicillin) which can lead to eradication rates of up to 80% (Malfertheiner, 1994). However, antibiotic treatment to eliminate *H. pylori* is not promising as a long-term solution since it has to be assumed that the bacteria will rapidly develop resistance to the antibiotics.

There is therefore a need for new forms of therapy to control a *H. pylori* infection and in particular for vaccines which are specifically directed against virulence factors of *H. pylori*. Virulence factors denote the properties of a pathogenic bacterium which enable it to colonize a particular ecological niche in the body of the host and to multiply there despite the immune response and the unspecific defence mechanisms of the host organism. Knowledge about virulence factors therefore aids in the better understanding of the course and mechanisms of an infectious disease. The most important previously examined virulence factors of *H. pylori* are urease, the flagella, the adhesins and the production of a cytotoxin.

Urease and enzyme on the surface of the bacteria is composed of two subunits (UreA, 26 kDa, UreB, 66 kDa) which constitute up to 5% of the total bacterial protein. Urease cleaves the urea which occurs in small concentrations in gastric juice into ammonia and carbon dioxide. According to the current perception the bacterium surrounds itself with a cloud of ammonia which leads to a local neutralization of the acid of the gastric juice. The extremely high motility of the bacteria can be attributed to the presence of polar flagella which enable the bacterium to move in the viscous mucous of the gastric mucous membrane and thus to reach the epithelial cell layer. The urease gene cluster (ureA-ureH) as well as the genes for the formation of the flagella (flaA, flaB) were cloned in *E. coli* and sequenced and isogenic mutants were constructed.

Approximately 50–60% of all isolated *H. pylori* strains produce a 87 kDa protein, the so-called vacuolising cytotoxin, which induces the formation of cytoplasmic vacuoles in in vitro cell cultures. The vacA gene which codes for the cytotoxin of *H. pylori* has also been cloned in the meantime and genetically characterized. Furthermore it is presumed that the cytotoxin-producing strains have a higher pathogenic potential than strains which do not produce this toxin. In addition a positive correlation was found between the production of the cytotoxin and the development of gastric ulcers.

Investigations on the adherence of *H. pylori* to epithelial cell lines in vitro show that the bacteria can bind to many cell lines of different tissues. In contrast *H. pylori* exhibits a very pronounced species and tissue selective adherence (tropism) in the host organism. Thus the bacteria are found only bound to epithelial cells which are of the gastral type of epithelial cells. This selectivity is explained by a specific interaction between a bacterial adhesin and a specific cellular receptor.

Up to now several potential adhesins of *H. pylori* have been described and a gene (hpaA) which codes for a so-called N-acetylneuraminyllactose-binding haemagglutinin was cloned and sequenced (Evans et al., 1993). This is a protein which should be able to recognize a receptor containing sialic acid on the epithelial cells. The significance of this adhesin for *H. pylori* infection is, however, controversial. Other potential adhesins are either only characterized by their molecular weight or their receptor binding specificity. These include a 63 kDa protein which appears to be homologous to the exoenzyme S of Pseudomonas aeruginosa an adhesin with ADP-ribosyl-transferase activity. Furthermore it is suspected that there is a yet unidentified adhesin which mediates a specific binding to the Lewis$^b$ blood group antigen of gastric epithelial cells (FalK et al., 1993; Borén et al., 1993).

Infection with *H. pylori* leads to a chronic inflammatory reaction of the gastric mucosa (gastritis). In addition a specific systemic immune response to *H. pylori* antigens is induced; the formation of secretory antibodies in the stomach (sIgA) has, however, not yet been indisputably clarified. As a result of the inflammation various immune cells are present in the gastric mucosa and submucosa e.g. polymorphonuclear leucocytes, monocytes, macrophages, lymphocytes and plasma cells (Blaser, 1992). In addition *H. pylori* activates neutrophils as well as monocytes and macrophages in vitro (Mai et al., 1991). Experiments with specific antibodies and complements show a rapid inactivation of *H. pylori* by neutrophils in vitro. However, in the in vivo situation these mechanisms do not lead to an inactivation of the pathogenic bacteria. How *H. pylori* survives for a long period in the host although it activates the aforementioned defence mechanism is unclear.

The host is not able to cope with the *H. pylori* infection under natural conditions. It was therefore even more surprising that the urease, an essential virulence factor of *H. pylori* (see above), has great potential as a vaccine (U.S. patent application U.S. Ser. No. 07/970,996 Urease-based vaccine against Helicobacter Infection).

In the *Helicobacter felis*/mouse model (*H. felis* is a Helicobacter species which naturally colonizes the stomach of the cat and can also infect the mouse) it was possible to show that oral vaccination of the *H. pylori* urease or the recombinant urease B subunit (rUreB) can protect mice against *H. felis* infection (preventive vaccine) and can also eliminate an infection which is already present (therapeutic vaccine) (Michetti et al., 1994; Corthesy-Theulaz et al., Gastroenterol., being printed). A decisive factor in the oral vaccination was the use of adjuvants such as e.g. cholera toxin which among others appears to be important for converting the immune reaction from the production of systemic antibodies to secretory antibodies.

The object of the present invention was to provide a method with which secretory genes from *Helicobacter pylori* which are potential candidates for vaccines can be identified in a simple and rapid manner.

This object is achieved by a method for identifying secretory genes from *Helicobacter pylori* wherein

| | |
|---|---|
| (a) | a gene bank of *H. pylori* DNA is set up in a host organism which contains an inducible transposon coupled to a marker for secretory activity, |
| (b) | the insertion of the transposon into the *H. pylori* DNA is induced and |
| (c) | the marker is used to select for clones which contain a secretory gene. |

The term "secretory gene" or "gene with secretory activity" is intended to denote a gene which codes for a secretory polypeptide i.e. for a polypeptide exported from the cytoplasm.

The method according to the invention is particularly suitable for identifying adherence genes from *H. pylori* in which in addition

| | |
|---|---|
| (d) | a retransformation of *H. pylori* with the DNA of clones of the gene bank, preferably with clones which contain genes with secretory activity, is carried out which produces isogenic *H. pylori* mutant strains by inteqration of the DNA into the chromosome and |
| (e) | adherence-deficient H. pylori mutant strains are selected. |

The method according to the invention enables adherence genes and the adherence proteins (adhesins) coded by them from *H. pylori* to be identified and isolated which are responsible for the specific interaction of the bacteria with the epithelial cells of the gastric mucosa. Since adhesins from *H. pylori* are usually only produced in very low amounts, it is usually extremely difficult to identify and isolate them by biochemical means. Moreover due to the tendency of *H. pylori* to spontaneously autolyse, cytoplasmic proteins are released and bind to the bacterial surface. In a biochemical purification such proteins have been erroneously identified as adhesins in the past (Doig et al., 1992; Doig et al, 1993).

The method according to the invention enables a rapid and simple identification of adhesins. In this method individual genes in the chromosome of *H. pylori* are inactivated with the aid of a transposon and mutants are produced which have defects in different chromosomal genes. Mutants can be selected from these independent defect mutants by specific selection of those mutants which are inactivated in adhesin genes and thus are no longer able to bind to receptors of the corresponding target cells.

The first step in the method according to the invention comprises setting up a gene bank of *H. pylori* DNA in a host organism, preferably a plasmid gene bank in a prokaryotic host organism such as *E. coli*. Subsequently the cloned *H. pylori* genes are mutagenized with the aid of a transposon which is coupled to a marker for secretory activity.

A particularly preferred transposon is the transposon TnMax9, which was deposited on the 26.05.95 at the "Deutsche Sammlung von Mikroorganismen und Zellkulturen GmbH (DSM)", Mascheroder-Weg 1b, De-38124 Braunschweig in an *E. coli* strain E 181 under the file number DSM 10008 according to the rules of the Budapest contract.

Figure 1:
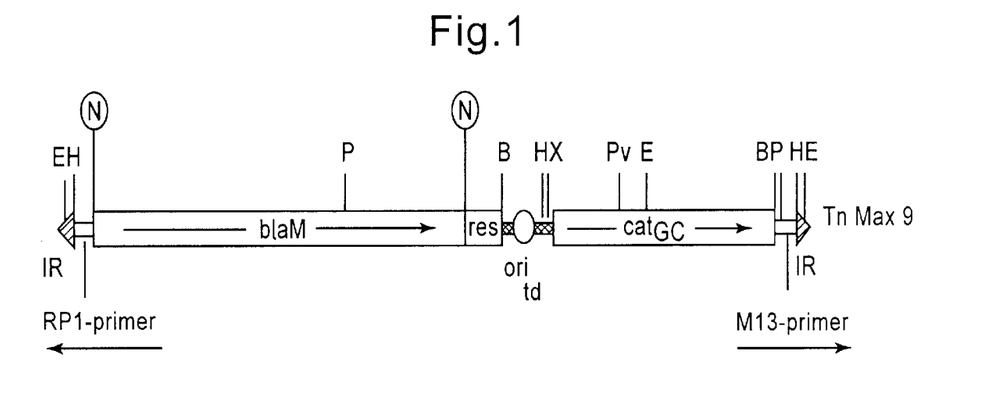

A schematic representation of TnMax9 is shown in FIG. 1. TnMax9 carries a copy of a β-lactamase gene without promoter and signal sequence (blaM) as a marker directly following the inverted repeats (IR) that delimit the actual transposon (Tadayyon and Broome-Smith, 1982). After insertion of TnMax9 the blaM gene fuses with the target gene and when the inactivated target gene is expressed a fusion protein between the target gene X and blaM is produced if the transposon is inserted in the correct orientation and in the correct reading frame with regard to the gene X. Provided the inactivated gene X codes for a secretory protein, in particular for a protein exported by the sec-dependent transport path (Pugsley, 1993), the fusion protein will be transported through the cytoplasmic membrane of the *E. coli* host cell into the periplasma. Here the fusion protein displays its activity (cleavage of β-lactam antibiotics) and thus mediates a resistance of the corresponding *E. coli* clone to the antibiotic Ampicillin.

However, if the gene X is a gene for a cytoplasmic protein it may also result in a fusion protein depending on the insertion (orientation, frame) but it does not exhibit any β-lactamase activity since β-lactamase is only active in the periplasmic environment but not in the cytoplasm. Thus this method can be used to identify specific mutants in genes which code for exported proteins by screening the mutants for β-lactamase activity after transposon mutagenesis in *E. coli*. Since the adhesin genes of *H. pylori* that are being sought after must also be export proteins, a special collection of *H. pylori* transposon mutants in genes which code for exported proteins can greatly reduce the number of mutants that have to be tested. In this manner the method according to the invention provides a greatly enriched mutant bank which can avoid a screening of a conventional mutant bank with ca. 2000–4000 clones which is very difficult to carry out in laboratory practice. The majority of the chromosomal genes of a bacterium that code for cytoplasmic proteins can be eliminated from the start by the selection step directed towards identifying secretory genes. Hence the number of *H. pylori* mutants that have to be tested on particular target cells for the loss of their ability to adhere can be reduced to an acceptable level for practical purposes.

The screening of bacterial adherence mutants can be carried out at various levels. Usually epithelial cell lines are used for this to which the bacteria specifically bind. In the case of *H. pylori* special gastric carcinoma cell lines can be used such as e.g. the KatoIII cell line (ATCC HTB 103) which has already been described by various authors as an adherence model (Clyne and Drumm, 1993). Although cell lines are relatively simple to handle and can usually be cultured in large amounts in vitro, it is not possible to fundamentally exclude changes in the quantitative and qualitative expression of surface proteins such as e.g. receptors due to the immortalization of the cells. Tissue models are therefore an alternative to this. In this case ultrathin sections are prepared from fixed tissue (microtome) which are incubated after saturation with the bacteria, Bacteria which do not bind to the receptors are washed away and the bound bacteria can be visualized with dyes (fluorescent dyes or special bacterial dyes). As a third step animal models may be used. These are in vivo experiments which can only be carried out if appropriate animal models for the microorganism are available.

The screening for adherence-defect *H. pylori* mutants is preferably first carried out with the aid of the KatoIII cell line. For this the mutants can be cultured on agar plates and subsequently labelled with the fluorescent dye fluorescein isothiocyanate (FITC). The labelled bacteria are then preferably added to the epithelial cells and incubated for 1 hour at 37° C. Subsequently a fluorescent microscope is used to examine whether the individual mutants are still able to bind to the epithelial cell line.

In a preferred embodiment of the method according to the invention the *H. pylori* gene bank is set up in a minimal plasmid vector which allows a selection for a transposon insertion in the vector DNA. The use of such minimal plasmid vectors greatly improves the efficiency of the mutagenesis procedure due to the small size of the genetic elements of the plasmid. Furthermore an insertion of the transposon into the vector DNA which is essentially only composed of the elements necessary for replication, selection and cloning, may probably lead to a loss of the ability of the vector to propagate in the host cell.

Moreover it is preferable to set up the *H. pylori* gene bank in a plasmid vector which contains a sequence suitable for conjugative transfer into other host organisms. An example of such a sequence is the oriT sequence (Fürste et al., 1989) the presence of which avoids the tedious isolation of plasmid DNA after inducing the transposon and transformation in suitable recipient cells.

The presence of an expression signal on the plasmid vector is also preferred to which the inserted *H. pylori* DNA is operatively linked. In this way it is possible to transcribe sequences of *H. pylori* genes which otherwise could not be transcribed due to the presence of specialized promoter sequences. In addition it is then also possible to transcribe genes which are organized into operons and which cannot be cloned as an entire unit. The use of a weak promoter is preferred since stronger promoters can lead to low transformation rates and even to deletions and transpositions of the cloned *H. pylori* sequences.

A particularly preferred plasmid vector is pMin2 (DSM 10007) which was deposited on 26.05.95 in the *E. coli* strain DH5α according to the rules according to the Budapest contract. The steps used to construct pMin2 are shown schematically in FIG. 2.

As already mentioned it is preferable for the method according to the invention that a conjugative transfer of plasmid DNA from the host organism into a recipient organism which allows selection for plasmids containing transposons is carried out in order to select for clones which contain a secretory gene.

The selection for adherence genes is preferably carried out by retransformation of *H. pylori* by which means a mutant strain is produced by integration of the DNA into the chromosome. Before this retransformation the marker gene e.g. blaM gene is preferably deleted in order to obtain a higher transformation rate, to avoid the production of *H. pylori* strains able to produce β-lactamase and to avoid possible interferences of the bacterial export apparatus by BlaM fusion proteins.

A further subject matter of the present invention is a gene bank of *H. pylori* DNA in a host organism which contains *H. pylori* DNA fragments inserted into a vector characterized in that the *H. pylori* genome is completely represented with a probability of over 90% and that the host organism in addition contains an inducible transposon coupled to a marker for secretory activity.

With a size of the *H. pylori* genome of 1.7 Mb (Bukanov and Berg, 1994) and an average size of the DNA insertion of preferably 3–6 kb especially preferably of ca. 4 kb, the gene bank according to the invention preferably comprises at least 400 clones per genome. Particularly preferably the gene bank comprises 2000 to 4000 clones.

The *H. pylori* DNA is preferably inserted into a plasmid vector especially preferably into a minimal plasmid vector as defined above. The host organism in which the gene bank is located is preferably a bacterium particularly preferably a gram-negative bacterium and most preferably *E. coli*.

The gene bank according to the invention can be used to identify secretory genes and in particular adherence genes from *Helicobacter pylori*.

It was possible to identify an adhesin gene from *H. pylori* denoted alpA and a polypeptide coded by this gene using the method according to the invention. Thus a subject matter of the present invention is also a DNA molecule which comprises

| | |
|---|---|
| (a) | the nucleotide sequence shown in SEQ ID NO:1 |
| (b) | a nucleotide sequence which corresponds to the sequence according to (a) within the scope of the degeneracy of the genetic code or |
| (c) | a nucleotide sequence which hybridizes with the sequences according to (a) or/and (b) under stringent conditions. |

In addition to the nucleotide sequence shown in SEQ ID NO:1 and a nucleotide sequence corresponding to this sequence within the scope of the degeneracy of the genetic code, the present invention also encompasses a DNA sequence which hybridizes with one of these sequences under stringent conditions. The term "hybridization" according to the present invention is used as described by Sambrook et al (Molecular Cloning. A Laboratory Manual, Cold Spring Harbor Laboratory Press (1989), 1.101 to 1.104). According to the present invention a hybridization under stringent conditions means that a positive hybridization signal is still observed after washing for 1 hour with 1×SSC and 0.1% SDS at 55° C. preferably at 62° C. and especially preferably at 68° C., in particular for 1 hour in 0.2×SSC and 0.1% SDS at 55° C. preferably at 62° C. and especially preferably at 68° C. The present invention encompasses a nucleotide sequence under such washing conditions hybridizing with one of the nucleotide sequences shown in SEQ ID NO:1 or with a corresponding nucleotide sequence within the scope of the degeneracy of the genetic code.

The DNA molecule according to the invention preferably codes for a polypeptide having the ability to adhere to human cells in particular to human gastric epithelial cells. In addition it is preferred that the DNA molecule according to the invention has a homology at the nucleotide level of at least 70%, particularly preferably of at least 80%, to the nucleotide sequence shown in SEQ ID NO:1. Furthermore it is preferred that the DNA molecule has a length of at least 15 preferably of at least 20 nucleotides.

A further subject matter of the present invention is a vector which contains at least one copy of a DNA molecule according to the invention. This vector can be any prokaryotic or eukaryotic vector on which the DNA sequence according to the invention is located preferably under the control of an expression signal (promoter, operator, enhancer etc.). Examples of prokaryotic vectors are chromosomal vectors such as for example bacteriophages (e.g. bacteriophage λ) and extrachromosomal vectors such as plasmids, whereby circular plasmid vectors are especially preferred. Suitable prokaryotic vectors are e.g. described by Sambrook et al., Supra, chapters 1 to 4.

On the other hand the vector according to the invention can also be a eukaryotic vector e.g. a yeast vector or a vector suitable for higher cells (e.g. a plasmid vector, viral vector, plant vector). Such vectors are for example described by Sambrook et al., Supra, chapter 16. Yet a further subject matter of the present invention is a cell which is transformed with a vector according to the invention. In a preferred embodiment the cell is a prokaryotic cell preferably a gram-negative prokaryotic cell particularly preferably an *E. coli* cell. However, on the other hand the cell according to the invention can also be a eukaryotic cell such as a fungal cell (e.g. yeast), an animal or a plant cell.

The invention also concerns a polypeptide which is coded by a DNA molecule according to the invention. The polypeptide is preferably capable of adhering to human cells and comprises (a) the amino acid sequence shown in SEQ ID NO:2 or (b) an amino acid sequence that immunologically cross-reacts with the sequence according to (a).

The polypeptide according to the invention preferably has a homology of at least 80% and most preferably of at least 90% to the amino acid sequence shown in SEQ ID NO:2.

The polypeptides according to the invention are preferably produced by transforming a cell with a DNA molecule or vector according to the invention, culturing the transformed cell under conditions in which expression of the polypeptide takes place and isolating the polypeptide from the cell or/and the culture supernatant. In this process the polypeptide according to the invention can be obtained as a fusion polypeptide as well as a non-fusion polypeptide.

The polypeptide according to the invention can also be used as an immunogen to produce antibodies. The present invention therefore also concerns an antibody which is directed against a polypeptide according to the invention. The antibody is preferably directed against the N-terminus e.g. the first 250 amino acids of the amino acid sequence shown in SEQ ID NO:2.

Yet a further aspect of the present invention concerns a pharmaceutical composition which contains a DNA molecule according to the invention, a polypeptide according to the invention or an antibody according to the invention as the active substance optionally together with common pharmaceutical auxiliary substances, diluents, additives and carriers.

The pharmaceutical composition according to the invention can be used on the one hand to diagnose a *Helicobacter pylori* infection. The diagnosis at the nucleic acid level is preferably carried out by using hybridization probes which contain a DNA according to the invention that is specific for the alpA gene or by amplification using DNA molecules according to the invention as primers. At the protein level the diagnostics are preferably carried out with the aid of the antibody according to the invention.

On the other hand the pharmaceutical composition can also be used to prevent or fight a *Helicobacter pylori* infection. For therapeutic application the polypeptide or parts thereof are used to produce an active vaccine or the antibody is used to produce a passive vaccine.

It is intended to further elucidate the invention by the following examples and figures.

| FIG. 1 | shows a linear restriction map of the transposon TnMax9 (DSM 10008) which was used to identify and inactivate the alpA gene. |
|---|---|
| FIG. 2 | shows a schematic representation of the construction of the minimal plasmid vectors pMin1 and pMin 2 (DSM 10007) which are suitable for an efficient transposon mutagenesis. |
| FIG. 3A | shows the selection principle of the transposon mutagenesis with Tnmax9 and the scheme for producing *H. pylori* mutants which have a defect in the secretory gene. |
| FIG. 3B | shows a schematic representation of the procedure for identifying *H. pylori* mutants which have a defect in a secretory gene. |
| FIG. 4 | shows a restriction map of the plasmid pMu140 which contains the regulatory region and the 5' end of the alpA gene (SEQ ID NO:1). The alpA gene is inactivated by insertion of the transposon TnMax9 (see triangle labelled TnMax9). When the plasmid is expressed an alpA-α-lactamase fusion protein is obtained. pMu140 is the original clone from the mutant gene bank from which the adherence-defect *H. pylori* strain P1-140 was obtained by retransformation and homologous recombination. |
| FIG. 5 | shows an immunoblot of *H. pylori* total cell lysates of the wild-type strain 69A (1) as well as the isogenic mutant strains P1-140 (2) and P1-179a (3). The wild-type strain 69A contains the alpA protein with a molecular weight of ca. 53 kDa. The alpa mutants P1-140 and P1-179a do not have A1pA protein. The immunoblot was developed using the antibody AB 202 which is directed against the N-terminus of the recombinant AlpA protein. |

SEQ ID NO:1 shows the nucleotide sequence of the *H. pylori* adherence gene alpA and the corresponding amino acid sequence.

SEQ ID NO:2 shows the amino acid sequence of the AlpA adherence polypeptide from *H. pylori*.

EXAMPLE 1
Construction of Minimal Vectors

The plasmid pRH144 was constructed by ligation of the ColE1 replication origin ($ori_{ColE1}$) and the tetracyclin resistance gene (Tet), which were both amplified as PCR fragments from pBR322 using the primer pairs RH104 (5'-AGC TGA ATT CAT GTT TGA CAT TGC CAT ATA GAT GAG CTT TAA TGC GGT AGT T-3') and RH105 (5'-AGC TCT GCA GCC GCC GGC TTC CAT TCA G-3') or RH106 (5'-AGC TCT GCA GAG ATC AAA GGA TCT TCT T-3') and RH107 (5'-TCT AGA ATT CGT ATC AGC TCA CTC AAA G-3').

pRH146 was constructed by Insertion of an oriT fragment which was obtained from the plasmid RP 4 (Marsh et al., 1984) by PCR amplification using the primer pair DF001 (5'-GTA CTG CAG CTT GGT TTC ATC AGC CA-3') and DF 002 (5'-GTA CTG CAG TTC AGT AAT TTC CTG CAT-3').

Subsequently the multiple cloning site of the plasmid pIC20R1 (Thomas, 1981) was inserted into the EcoRI site of pRH146. In order to obtain the plasmid pMin1 the polylinker of pRH146 was replaced by a double-stranded synthetic polylinker region which was cloned into the EcoRI site of pRH146 and was composed of the two partially complementary oligonucleotides RH117 (5'-AAT TAG ATC ATT AAA GGC TCC TTT TGG AGC CTT TTT TGA ATT CAG ATC TCG AGG TAC CCG GGA TCC TCT AGA-3') and RH118 (5'-AAT TAG ATC AAA AAA AAA GCC CGC TCA TTA GGC GGG CTA AGC TTG TCG ACA TCG ATC TAG AGG ATC CCG GGT ACC-3').

The flanking EcoRI sites were destroyed by the cloning procedure. The cloned polylinker region contained the transcription terminators of the phage fd ($ter_{fd}$) and the trpA gene ($ter_{trpA}$)

In order to obtain the plasmid pMin2 the promoter of the iga gene (Piga) derived from gonococci was amplified as a PCR fragment from the plasmid pIP 100 (Pohlner et al., 1987) using the oligonucleotides S0009 (5'-GGA TCC GAA TTC TCA TGT TTG ACA G-3') and S0010 (5'-GTC GAC AGA TCT TTT AAT AGC GAT AAT GT-3'). The amplification fragment was ligated into the EcoRI and BglII sites of pRH160. The trpA terminator was removed by replacing the BglII/BamHI fragment of pMin1 by the corresponding fragment of pRH146.

Figure 2:
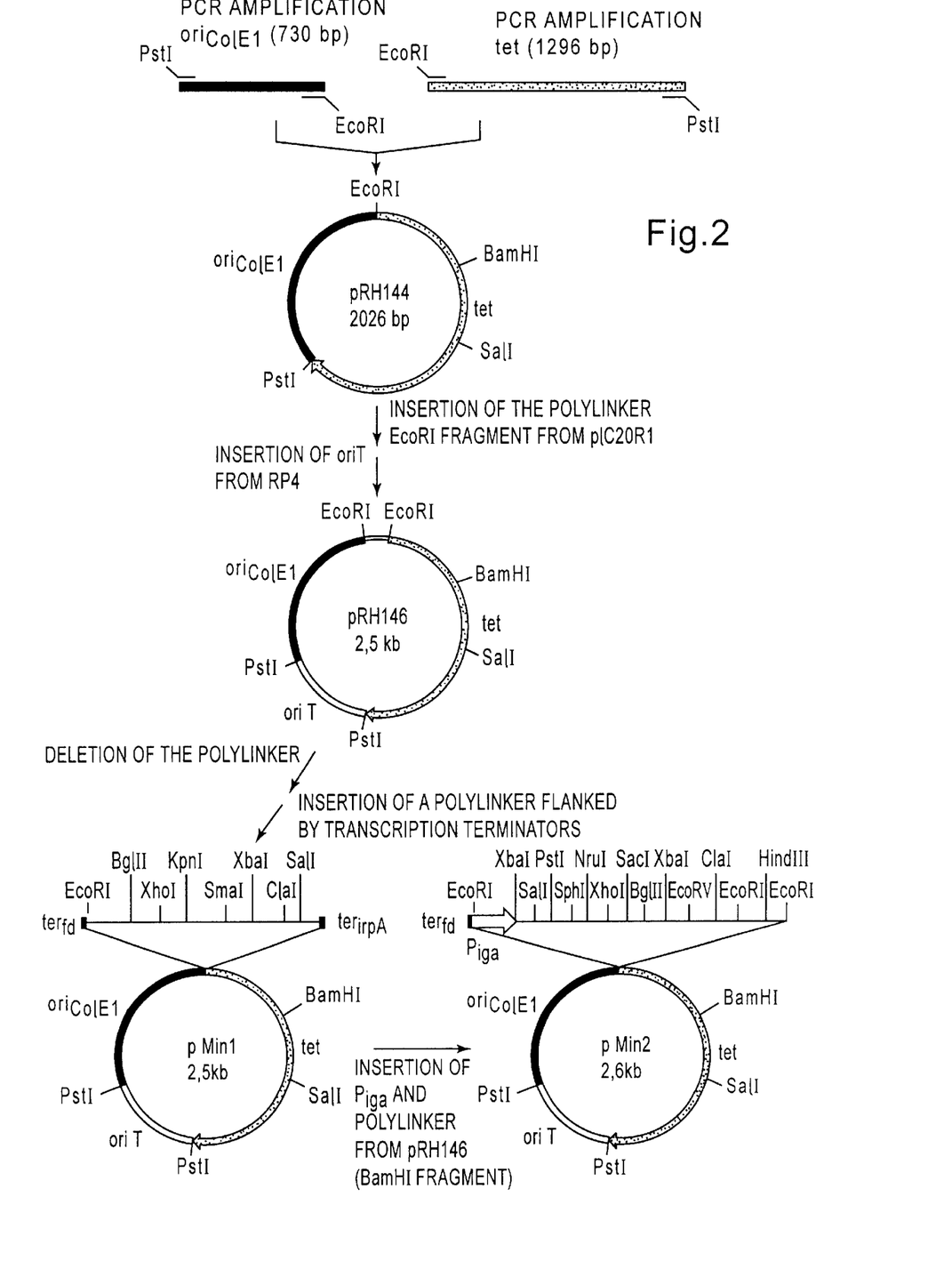

The construction scheme for pMin1 and pMin2 is shown in FIG. 2. The *E. coli* strain DH5α containing the plasmid pMin was deposited at the DSM under the file number 10007.

EXAMPLE 2
Construction of the Transposon TnMax9

The plasmid pRH110 which is a derivative of pTnax1 (Haas et al., 1993) with a SalI linearized pIC20R2 vector in the singular SalI cleavage site was used as the basis for the construction of pTnMax9. Subsequently the central region of TnMax1 ($ori_{fd}$-res-$cat_{GC}$) was deleted by HindIII cleavage and religation. The sequences for the M13-forward (M13 primer) and M13 reverse (M13-RP1) sequencing primer were introduced (ligation) into the HindIII cleavage site of pRH110 by insertion of the two partially complementary oligonucleotides RH096 (5'-AGC TTA CTG GCC GTC GTT TTA CAG CGG CCG CAG GAA ACA GCT ATG ACC GA-3') and RH097 (5'-AGC TTC GGT CAT AGC TGT TTC CTG CGG CCG CTG TAA AAC GAC GGC CAG TA-3'). The resulting plasmid pRH140 contained a singular NotI restriction cleavage site between the two primer binding sites. The res DNA fragment of Tn1721 was amplified from the plasmid pJOE106 (Schöffl et al., 1981) with the aid of the oligonucleotide primer pair RH098 (5'-AGA AGC GGC CGC AAA AGG ATC CAT AGG TGC AAG CAA GTT A-3') and RH099 (5'-AGC TGC GGC CGC AAA AAG ATC TCA AAG CCC ATT TCT GTC AGG-3') and inserted into the pRH140 NotI cleavage site. As a result the plasmid pRH141 was formed which had singular BamHI and BglII restriction cleavage sites left and right of res. Now the replication origin ($ori_{fd}$) together with the $cat_{GC}$ resistance was isolated from pRH42 as a BamHI fragment and ligated into the BamHI cleavage site of pRH141. Deletion of the pIC20R2 vector (with SalI) finally led to pTnMax5 the base construct for all further TnMax transposons. Finally the β-lactamase gene without a promoter and without a signal sequence (blaM gene) from the plasmid pBR322 (Sutcliffe, 1979) was amplified by means of PCR with the aid of the oligonucleotides RH124 (5'-AGT TGC GGC CGC ACC CAG AAA CGC TGG TG-3') and RH127 (5'-AGC TAG ATC TAG ATT ATC AAA AAG GAT C-3') and inserted into the NotI and BglII cleavage sites of TnMax5 which resulted in pTnMax7. The NotI cleavage site between $cat_{GC}$ and the inverted repeat (IR) of pTnMax7 was removed by filling up the overhanging ends with Klenow polymerase. The BglII cleavage site at the 3' end of blaM was converted into a NotI cleavage site by insertion of the complementary oligonucleotide pair S0012 (5'-GAT CAA GTC GCG GCC GCC TGA T-3') and S0013 (5'-GAT CAT CAG GCG GCC GCG ACT T-3') which led to the transposon derivative pTnMax9.

The *E. coli* strain E 181 containing the transposon derivative pTnMax9 was deposited at the DSM under the file number 10008.

EXAMPLE 3
Construction of a *H. pylori* Plasmid Gene Bank

A plasmid gene bank of the chromosomal DNA of the *H. pylori* wild-type strain 69A was set up. For this the chromosomal DNA was isolated by the method of Leying et al. (1992) from *H. pylori* and partially cleaved with each of the restriction endonucleases Sau3AI and HpaII. Subsequently the DNA fragments were separated on a preparative agarose gel and fragments of 3–6 kb were eluted from the gel. These DNA fragments were ligated into the plasmid vector pMin2 which was specially constructed for this purpose which had been cleaved with the restriction enzymes BglII and ClaI, ligated (T4 ligase) and the ligation mixture was transformed into the *E. coli* strain E 181 which is a derivative of the strain HB101 (Bayer and Roulland-Dussoix, 1969) containing the lysogenes λphages λCH616 and had already been transformed with the transposon TnMax9. In this process ca. 2400 independent transformants were obtained.

EXAMPLE 4
Isolation of *H. pylori* Mutants

Figure 3:
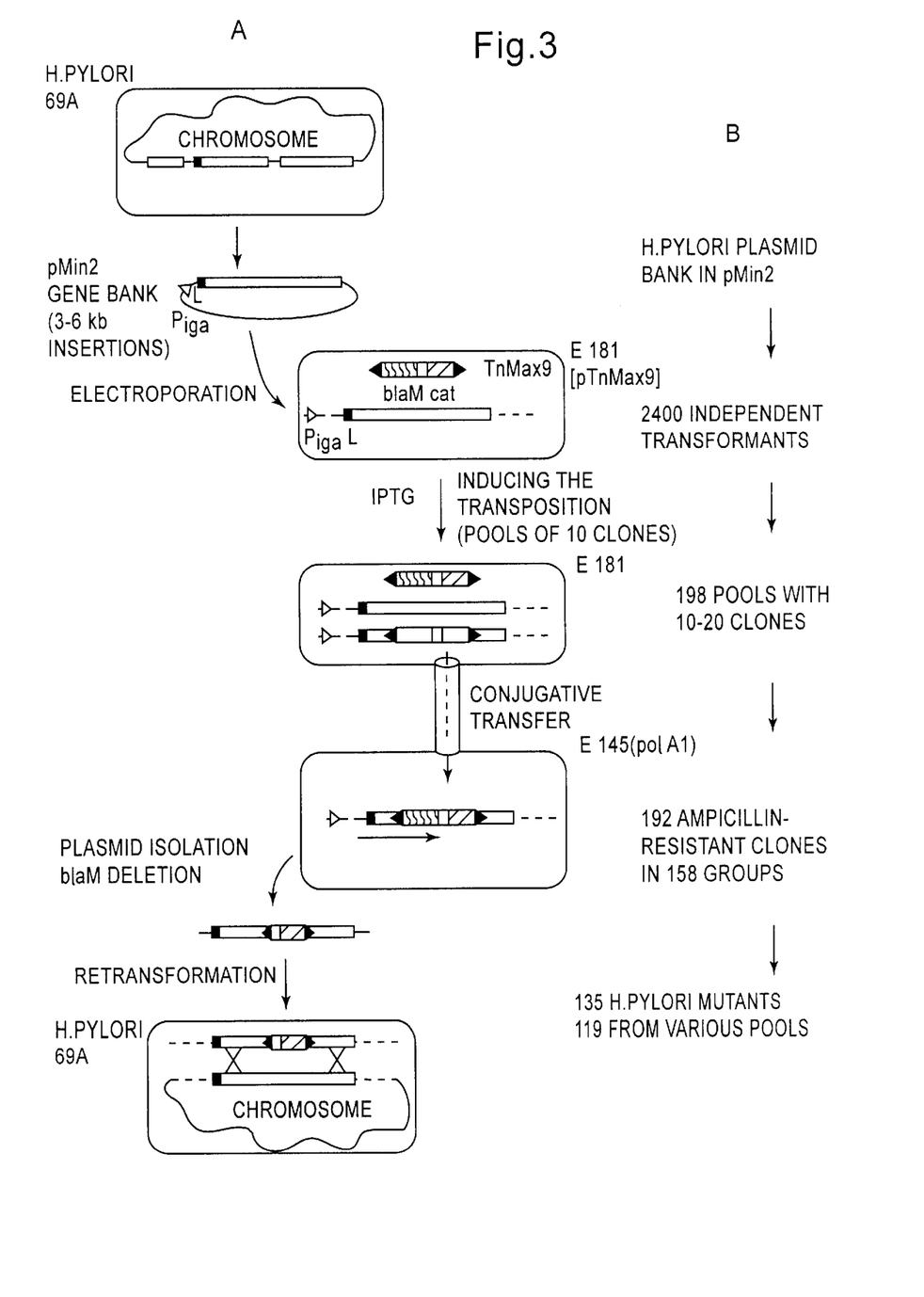

The selection principle of the mutagenesis and the procedure for identifying mutants are shown schematically in FIG. 3A and 3B.

In order to carry out the transposon mutagenesis 10 transformants were pooled in each case and mutually induced by which means a total of 190 pools each with 10–20 clones were treated further. 191 ampicillin resistant *E. coli* plasmid clones were isolated from this mutagenesis which carried independently mutated *H. pylori* genes. These 192 plasmids were isolated from *E. coli* and used for the retransformation of the *H. pylori* strain 69A. 135 *H. pylori* mutants were isolated from these 192 transformations which were presumably mutated in genes which code for secretory proteins. The *H. pylori* mutant collection was then tested in a screening assay for *H. pylori* mutants which had lost their ability to bind to KatoIII epithelial cells.

For this the mutants were labelled with FITC and cultured for 1 hour at 37° C. together with the epithelial cells. The test for adherence was carried out directly by observation with a fluorescence microscope. 2 mutants were found in this case (No. P1-140 and P1-179a) which showed a greatly reduced adherence.

Both mutants also exhibited no adherence in the second adherence model, the tissue sections of human stomach. The *H. pylori* wild-type strain as well as all other mutants also showed a strong adherence in this model.

Figure 4:
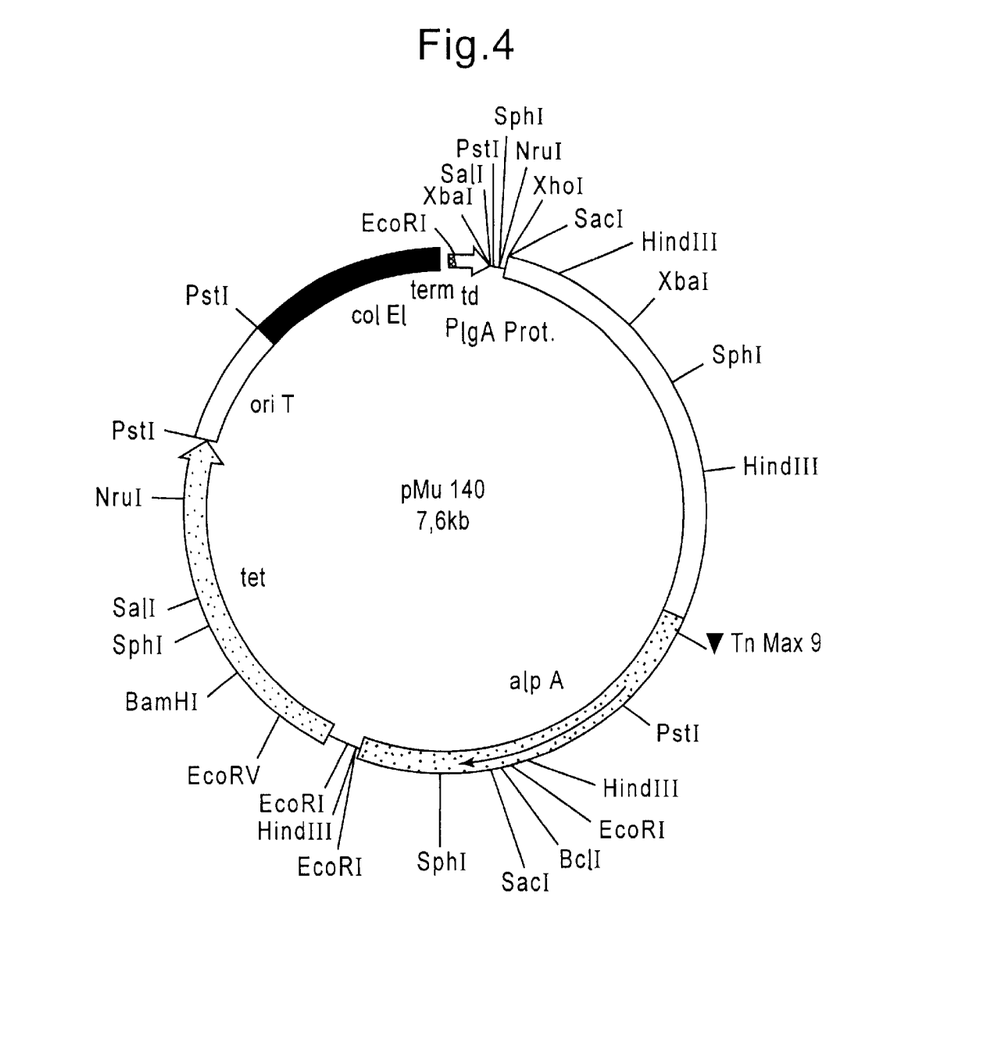

The plasmid pMu140 used to produce the mutant strain P1-140 is shown in FIG. 4. The plasmid pMU179a (not shown) was used to produce the mutant strain P1-179a. Independent transformations of both plasmids in *H. pylori* 69A led to the identified adherence defect which proves that no secondary mutations had occurred in the bacterial chromosome but rather that the TnMax9 insertion in the cloned adhesin gene led to the observed phenotype of the *H. pylori* mutants. The mapping and sequencing of the genes of the plasmid clones pMu140 and pMu179 inactivated by the transposon TnMax9 showed that both clones were the same gene; the transposon was only inserted at different sites. Since the coded protein is a lipoprotein i.e. a protein which is anchored in the membrane with a lipid anchor, the corresponding gene was denoted alpA (adherence associated lipoprotein A). Our data from computer secondary structure predictions of membrane proteins and of certain conserved protein sequences at the C-terminus of the protein (C-terminal phenylalanine; Struyvé et al., 1991) argue in favour of an integral membrane protein incorporated into the outer membrane of the gram-negative bacteria.

EXAMPLE 5
Expression of the AlpA Gene and Production of Antibodies

Figure 5:
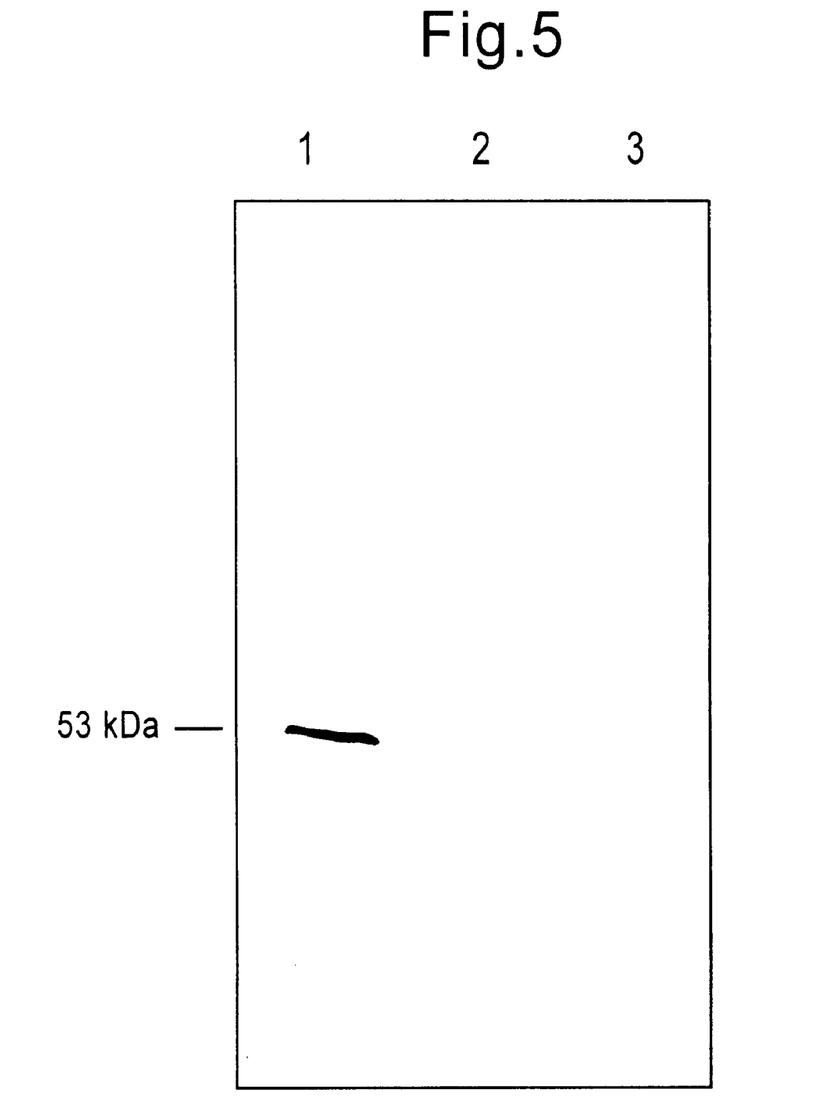

A fusion protein was then produced with the aid of the pEV40 *E. coli* expression system (Pohlner et al., 1993) which comprises ca. 50% of the N-terminus of AlpA and an N-terminal histidine tag. This was used to purify the fusion protein by chelate affinity chromatography with a $Ni_2$ agarose column and used to obtain an antiserum from the mouse. This antiserum which is denoted AK202 recognized the AlpA protein as a 53 kDa protein in an immunoblot of a *H. pylori* total cell lysate. As expected the 53 kDa AlpA protein was not detectable in an immunoblot in the case of the *H. pylori* mutants P1-140 and P1-179a (see FIG. 5). The test that AlpA is a lipoprotein was carried out by a specific palmitylation of the AlpA-β-lactamase fusion protein which was formed by the original insertion of TnMax9 in alpA.

Literature

Alper, J. (1993) Ulcers as an infectious disease. Science 260: 159–160.

Bizzozero, G. (1893) Ueber die schlauchförmigen Drusen des Magendarmkanals und die Beziehungen ihres Epithels zu dem Oberflächenepithel der Schleimhaut. Arch Mikr Anast 42: 82.

Blaser, M. J. (1992) Hypothese on the pathogenesis and natural history of *Helicobacter pylori* induced inflammation. Gastroenterol 102: 720–727.

Borén, T., Falk, P., Roth, K. A., Larson, G., Normark, S. (1993) Attachment of *Helicobacter pylori* to gastric epithelium mediated by blood group antigens. Science 262: 1892–1895.

Boyer, H. W. and Roulland-Dussoix, D. (1969) A complementation analysis of the restriction and modification of DNA in *Escherichia coli*. J. Mol. Biol. 41: 459–472.

Bukanov, N. O., Berg, D. E. (1994) Ordered cosmid library and high-resolution physical-genetic map of *Helicobacter pylori* strain NCTC11638. Mol Microbiol 11: 509–523.

Clyne, M., Drumm, B. (1993) Adherence of *Helicobacter pylori* to primary human gastrointestinal cells. infect Immun 61: 4051–4057.

Doig, P., Austin, J. W., Kostrzynska, M., Trust, T. J. (1992) Production of a corserved adhesin by the human gastroduodenal pathogen *Helicobacter pylori*. J. Bacteriol 174: 2539–2547.

Doig, P., Austin, J. W., Trust, T. J. (1993) The *Helicobacter pylori* 19.6-kilodalton protein is an intron-containing protein resembling ferritin. J. Bacteriol 175: 557–560.

Evans, D. G., Karjalainen, T. K., Evans, D. J., Jr., Graham, D. Y., Lee, C.—H. (1993) Cloning, nucleotide sequence, and expression of a gene encoding an adhesin subunit protein of *Helicobacter pylori*. J. Bacterial 174: 674–683.

Falk, P., Roth, K. A., Boren, T., Westblom, T. U., Gordon, J. I., Normark, S. (1993) An in vitro adherence assay reveals that *Helicobacter pylori* exhibits cell lineage-specific tropism in the human gastric epithelium. Proc. Natl. Acad. Sci USA 90: 2035–2039.

Fürste, J. P., Pansegrau, W., Ziegelin, G., Kröger, M. and Lanka, E. (1989) Conjugative transfer of promiscuous IncP plasmids: interaction of plasmid-encoded products with the transfer origin. Proc. Natl. Acad. Sci USA 86: 1771–1775.

Goodwin, C. S., Armstrong, J. A., Chilvers, T., Peters, M., Collins, M. D., Sly, L., McConnell, W., Harper, W. E. S. (1989) Transfer of *Campylobacter pylori* and *Campylobacter mustelae* to Helicobacter gen. nov. as *Helicobacter pylori* comb. nov. and *Helicobacter mustelae* comb. nov., respectively. Int. J. Syst. Bact 39: 397–405.

Haas, R., Kahrs, A. F., Facius, D., Allmeier, H., Schmitt, R., Meyer, T. F. (1993) TnMax- a versatile mini-transposon for the analysis of cloned genes and shuttle mutagenesis. Gene 130: 23–31.

Isaacson, P. G., Spencer, J. (1993) Is gastric lymphoma an infectious disease? Hum. Pathol. 24: 569–570.

Lee, A., Fox, J., Hazell, S. (1993) Pathogenicity of *Helicobacter pylori*: a perspective. Infect. Immun. 61: 1601–1610.

Leying, H., Suerbaum, S., Geis, G., Haas, R. (1992) Characterisation of flaA, a *Helicobacter pylori* flagellin gene. Mol. Microbiol 6: 2863–2874.

Mai, U. E. H., Perez-Perez, I., Wahl, L. M., Wahl, S. M., Blaser, M. J., Smith, P. D. (1991) Soluble surface proteins from *Helicobacter pylori* activate monocytes/macrophages by lipopolysaccharide-independent mechanism. J. Clin Invest. 87: 894–900.

Malfertheiner P. (1994) *Helicobacter pylori*—Von der Grundlage zur Therapie. Bayerdörfer E., Birkholz S., B örsch G. et al., (eds.) Stuttgart, New York: Georg Thieme Verlag; p. 1–104.

Marsh, J. E., Erfle, M. and Wykes, E. J. (1984) The pIC plasmid and phage vectors with versatile cloning sites for recombinant selection by insertional inactivation. Gene 32: 481–485.

Marshall, B. J., Royce, J., Annear, D. I., Goodwin, C. S., Pearman, J. W., Warren, J. R., Armstrong, J. A. (1984) Original isolation of Campylobacter pyloridis from human gastric mucosa. Microbios. Lett. 25: 83–88.

Michetti, P., Corthesy-Theulaz, I., Davin, C., Haas, R., Vaney, A. C., Heitz, M., Bille, J., Kraehenbuhl, J. P., Saraga, E., Blum, A. L. (1994) Immunization of Balb/c mice against *Helicobacter felis* infection with *Helicobacter pylori* urease. Gastroenterol 107: 1002–1011.

Nomura, A., Stemmermann, G. N., Chyou, P. H., Kato, I., Perez-Perez, G. I., Blaser, M. J. (1991) *Helicobacter pylori* infection and gastric carcinoma among japanese americans in Hawaii. N Engl. J. Med. 325: 1132–1136.

Parkin, D. M., Laara, E., Muir, C. S. (1988) Estimates of the worldwide frequency of sixteen major cancers in 1980. Int. J. Cancer 41: 184–197.

Parsonnet, J., Friedmann, G. D., Vandersteen, D. P., Chang, Y., Vogelman, J. H., Orentreich, N., Sibley, R. K. (1991) *Helicobacter pylori* infection and the risk of gastric carcinoma. N. Engl. J. Med. 325: 227–1231.

Pohlner, J., Kramer, J. and Meyer, T. F. (1993) A plasmid system for high-level expression and in vitro processing of recombinant proteins. Gene 130: 121–126.

Pohlner, J., Halter, R., Beyreuther, K. and Meyer, T. F. (1987) Gene structure and extracellular secretion of Neisseria gonorrhoeae IgA protease. Nature 325: 458–462.

Pugsley, A. P. (1993) The complete general secretory pathway in gram-negative bacteria. Microbiol Rev. 57: 50–108.

Schöffl, F., Pühler, A., Altenbuchner, J. and Schmitt, R. (1981) The tetracycline resistance transposons Tn1721 and Tn1771 have three 38-base-pair repeats and generate five-base-pair repeats. Mol. Gen. Genet 181: 87–94.

Sipponen, P. (1992) Natural history of gastritis and its relationship to peptic ulcer disease. Digestion 51: 70–75.

Sipponen, P., Hyvärinen, H. (1993) Role of *Helicobacter pylori* in the pathogenesis of gastritis, peptic ulcer and gastric cancer. Scand. J. Gastroenterol 28: 3–6.

Solnick, J. V., Tompkins, L. S. (1993) *Helicobacter pylori* and gastroduodenal disease: pathogenesis and host-parasite interaction. Infect Ag Dis 1: 294–309.

Stolte, M., Eidt, S. (1993) Healing gastric MALT lymphomas by eradicating *H. pylori*. Lancet 342: 568.

Struyvé, M., Moons, M., Tommassen, J. (1991) Carboxy-terminal phenylalanine is essential for the correct assembly of a bacterial outer membrane protein. J. Mol. Biol. 218: 141–148.

Sutcliffe, J. G. (1979) Complete nucleotide sequence of the *Escherichia coli* plasmid pBR322. Cold spring Harb. Symp. Quant Biol. 43: 77–90.

Tadayyon, M., Broome-Smith, J. K. (1992) TnblaM—a transposon for directly tagging bacterial genes encoding cell envelope and secreted proteins. Gene 111: 21–26.

Taylor, D. N., Blaser, M. J. (1991) The epidemiology of *Helicobacter pylori* infection. Epidemiol Rev. 13: 42–59.

Thomas C. M. (1981) Molecular genetics of broad host range plasmid RK2. Plasmid 5: 10–19.

Warren, J. R., Marshall, B. (1983) Unidentified curved bacilli on gastric epithelium in active chronic gastritis. Lancet i: 1273–1275.

What is claimed is:

1. An isolated and purified Helicobacter-specific DNA molecule, consisting of
   (a) the nucleotide sequence shown in SEQ ID NO:1;
   (b) a nucleotide sequence which encodes an amino acid sequence as shown in SEQ ID NO:2; or
   (c) a nucleotide sequence which hybridizes with a sequence which is complementary to a sequence according to (a) under stringent conditions, wherein said stringent conditions comprise washing for one hour with 1×SSC and 0.1% SDS at 55° C., and wherein said nucleotide sequence codes for a polypeptide with the ability to adhere bacteria to human cells.

2. The DNA molecule as claimed in claim 1, parts (a) and (b), wherein it codes for a polypeptide with the ability to adhere bacteria to human cells.

3. A vector comprising at least one copy of the DNA molecule as claimed in claim 1.

4. A cell transformed with the vector as claimed in claim 3.

5. An isolated and purified polypeptide coded by the DNA molecule as claimed in claim 1 and wherein said polypeptide is capable of adhering to human cells.

6. A composition comprising the polypeptide of claim 5 the active substance, and at least one member selected from the group consisting of a diluent, additive, and carrier.

7. The polypeptide according to claim 5, wherein said polypeptide comprises
   (a) the amino acid sequence shown in SEQ ID NO: 2, or
   (b) immunogenic fragments thereof, wherein said fragments are capable of adhering to human cells.

8. A process for the production of a polypeptide capable of adhering to human cells, comprising transforming a cell with the DNA molecule as claimed in claim 1 to produce a transformed cell, culturing the transformed cell under conditions in which an expression of the polypeptide takes place and isolating the polypeptide from the cell or the culture supernatant, or from the cell and the culture supernatant.

9. A composition comprising the DNA molecule of claim 1 as the active substance, and at least one member selected from the group consisting of a diluent, additive, and carrier.

10. A recombinant DNA construct comprising an isolated and purified Helicobacter-specific DNA molecule, wherein said DNA molecule comprises
    (a) the nucleotide sequence shown in SEQ ID NO:1;
    (b) a nucleotide sequence which encodes an amino acid sequence as shown in SEQ ID NO:2; or
    (c) a nucleotide sequence which hybridizes with a sequence which is complementary to a sequence according to (a) under stringent conditions where said stringent conditions comprise washing for one hour with 1×SSC and 0.1% SDS at 55° C., and wherein said nucleotide sequence codes for a polypeptide with the ability to adhere bacteria to human cells.

11. The recombinant DNA construct of claim 10, wherein said DNA molecule comprises
    (a) the nucleotide sequence shown in SEQ ID NO:1; or
    (b) a nucleotide sequence which encodes an amino acid sequence as shown in SEQ ID NO:2;
       wherein said DNA molecule codes for a polypeptide with the ability to adhere bacteria to human cells.

12. A cell transformed with the recombinant DNA construct of claim 10.

13. A process for the production of a polypeptide having the ability to adhere to human cells, comprising transforming a cell with the DNA molecules as claimed in claim 10 to produce a transformed cell, culturing the transformed cell under conditions in which an expression of the polypeptide takes place and isolating the polypeptide from the cell or the culture supernatant, or from the cell and the culture supernatant.

* * * * *